(12) United States Patent
Twydell et al.

(10) Patent No.: US 6,979,453 B1
(45) Date of Patent: *Dec. 27, 2005

(54) PESTICIDAL COMPOSITIONS COMPRISING AN AERATED GEL CONTAINING HYDROPHOBIC SILICA

(75) Inventors: Roland Twydell, Widnes (GB); Lesley Le Quesne, Widnes (GB)

(73) Assignee: Sorex Limited, Widnes (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/130,438

(22) PCT Filed: Nov. 15, 2000

(86) PCT No.: PCT/GB00/04341

§ 371 (c)(1),
(2), (4) Date: Aug. 23, 2002

(87) PCT Pub. No.: WO01/35744

PCT Pub. Date: May 25, 2001

(30) Foreign Application Priority Data

Nov. 18, 1999 (EP) .................................. 99309191

(51) Int. Cl.⁷ ............................................. A01N 25/32

(52) U.S. Cl. ..................... 424/406; 424/421; 424/724; 504/187

(58) Field of Search ................... 424/484, 485, 424/405–408, 409, 421, 724, 417; 504/101, 504/187

(56) References Cited

U.S. PATENT DOCUMENTS

| | | | |
|---|---|---|---|
| 3,159,536 A | 12/1964 | Marotta | 167/42 |
| 4,008,170 A | 2/1977 | Allan | 252/194 |

(Continued)

FOREIGN PATENT DOCUMENTS

| | | |
|---|---|---|
| DE | 198 19 856 A1 | 11/1999 |
| EP | 0 478 326 A1 | 4/1992 |
| FR | 1 438 271 A | 7/1966 |
| JP | 09241102 * | 9/1997 |

(Continued)

OTHER PUBLICATIONS

Database WPI, Section Ch, Derwent Publications Ltd., London, GB; AN 1970-31920R, JP 45 012154B (Koburu Laboratory) (abstract).

(Continued)

*Primary Examiner*—Neil S. Levy
(74) *Attorney, Agent, or Firm*—Edwards & Angell, LLP; Peter C. Lauro, Esq.

(57) ABSTRACT

A pesticidal composition comprises, as the sole pesticidally active component, a storage-stable aerated gel composition comprising 30 to 97% by weight of water, 0.2 to 5% by weight of a gelling agent selected from xanthan gum, sodium alginate and neutralized carboxyvinyl polymer and 2 to 5% by weight of fine particulate, hydrophobic silicone-treated silica having a surface area of from 80 to 300 m²/g. The composition is in the form of fine particles of an aqueous gel containing the water and gelling agent, the surfaces of which fine particles are coated with a coating of the finely particulate hydrophobic silica. The composition is useful in a method of controlling pests, particularly insects and acarids.

20 Claims, 4 Drawing Sheets

U.S. PATENT DOCUMENTS

| | | | |
|---|---|---|---|
| 4,274,883 A | 6/1981 | Lumbeck et al. | |
| 5,122,518 A | 6/1992 | Vrba | 514/63 |
| 5,192,545 A * | 3/1993 | Nakashima | 424/405 |
| 5,342,597 A | 8/1994 | Tunison, III | |
| 5,556,453 A | 9/1996 | LaBrash et al. | |
| 5,714,122 A | 2/1998 | Bretscher et al. | |
| 5,800,603 A | 9/1998 | Cruslock et al. | |
| 5,846,454 A | 12/1998 | Koczo et al. | |
| 6,716,885 B1 | 4/2004 | Twydell et al. | |

FOREIGN PATENT DOCUMENTS

| | | | |
|---|---|---|---|
| JP | 11228346 | * | 8/1999 |
| WO | WO 94/09626 | | 5/1994 |
| WO | WO 94/09626 A | | 5/1994 |

OTHER PUBLICATIONS

Database WPI, Section Ch, Derwent Publications Ltd., London, GB; AN 1971-31674S, JP 46 016947B (Koburu Lab KK) (abstract).

Cab-O-Sil TS 720; Treated Fumed Silica (Brochure); CABOT; 36 pgs.

Database WPI, Section Ch, Derwent Publications Ltd., London, GB; AN 1970-41634R, JP 45 016232 B (Koburu Laboratory KK) (abstract).

* cited by examiner

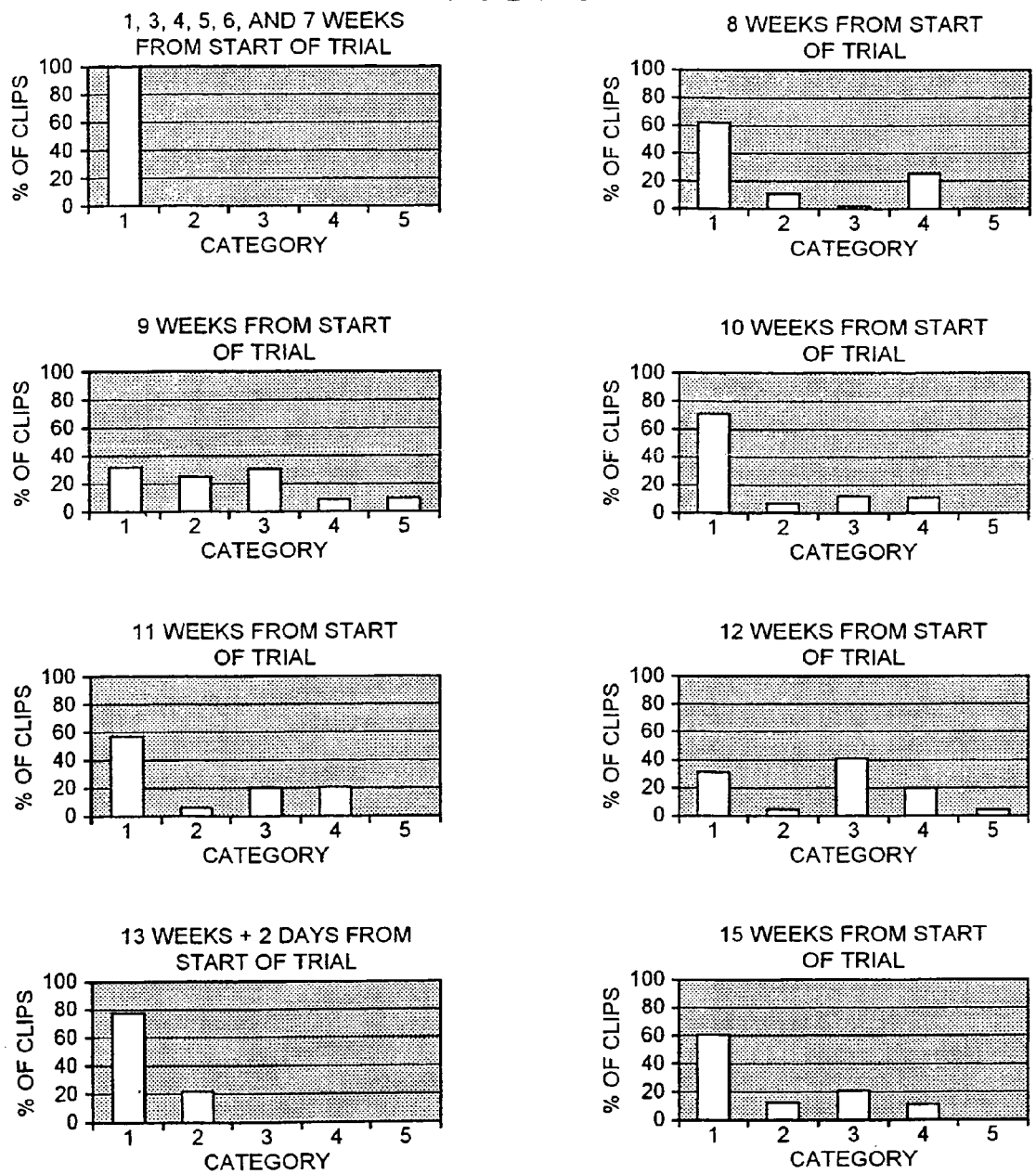

PESTICIDAL COMPOSITIONS COMPRISING AN AERATED GEL CONTAINING HYDROPHOBIC SILICA

This application is a U.S. national phase application pursuant to 35 U.S.C. §371 of international application no. PCT/GB00/04341, filed Nov. 15, 2000, which designated the United States and was published in English on May 25, 2001 under publication number WO 01/35744 A1, and which claims priority under 35 U.S.C. § 119 to EP 99309191.7 filed Nov. 18, 1999.

The present invention relates to pesticidal compositions comprising an aerated gel containing hydrophobic silica. More particularly, it relates to pesticidal compositions containing hydrophobic silica, water and a gelling agent and to a method of controlling pests, such as insects and acarids, using such compositions.

Aqueous dispersions of silica can be prepared into a state known generally in the prior art as "dry water". In fact, "dry water" is known in two forms. The first form can be produced by absorbing aqueous liquids onto hydrophilic material to form a material which exists as free-flowing powder or granules. The second form can be produced by coating finely divided aqueous liquids with powdered hydrophobic material, such as metal oxides. Each liquid particle in this second form of "dry water" is separated from the next by a hydrophobic metal oxide coating and by air spaces. Very high speeds of, for example, over 6000 rpm, and mixing times of 15 minutes are typically required. This second form is, however, thermodynamically unstable and, when produced, tends to break down after a relatively short period of time.

A method of controlling insects and other pests using a dry water composition containing pyrogenically produced hydrophobic silica is disclosed in U.S. Pat. No. 5,122,518. The dry water composition disclosed in the prior art, however, is unstable and cannot be stored for long periods of time. Also, when the prior art composition is applied using conventional spraying apparatus it causes blocking of the nozzles of the apparatus and cannot be sprayed over distances comparable to those achieved using a sprayable liquid.

The present invention is based on the discovery that stable aerated gels analogous to "dry water" compositions can be used for the control of pests. These stable aerated gels can be sprayed, using conventional spraying equipment, like liquids and, thus, can be sprayed over large distances without causing blocking of the nozzles of the spraying equipment.

The present invention provides a pesticidal composition comprising, as the sole pesticidally-active component, a storage-stable aerated gel composition comprising 30 to 97% by weight of water, 0.2 to 5% by weight of a gelling agent selected from xanthan gum, sodium alginate and neutralised carboxyvinyl polymer and 2 to 5% by weight of a fine particulate, hydrophobic silicone-treated silica having a surface area of from 80 to 300 $m^2/g$ which said composition is in the form of fine particles of an aqueous gel containing the water and gelling agent, the surfaces of which fine particles are coated with a coating of the finely particulate hydrophobic silica.

The present invention further provides a method of controlling pests which comprises contacting the pests with a storage-stable aerated gel composition comprising 30 to 97% by weight of water, 0.2 to 5% by weight of a gelling agent selected from xanthan gum, sodium alginate and neutralised carboxyvinyl polymer and 2 to 5% by weight of a fine particulate, hydrophobic silicone-treated silica having a surface area of from 80 to 300 $m^2/g$ which said composition is in the form of fine particles of an aqueous gel containing the water and gelling agent, the surfaces of which fine particles are coated with a coating of the finely particulate hydrophobic silica.

BRIEF DESCRIPTION OF THE DRAWINGS

FIG. 4 shows the results of clip assessments described in Experiment 6 using Littac against poultry red mite.

Figure 1:
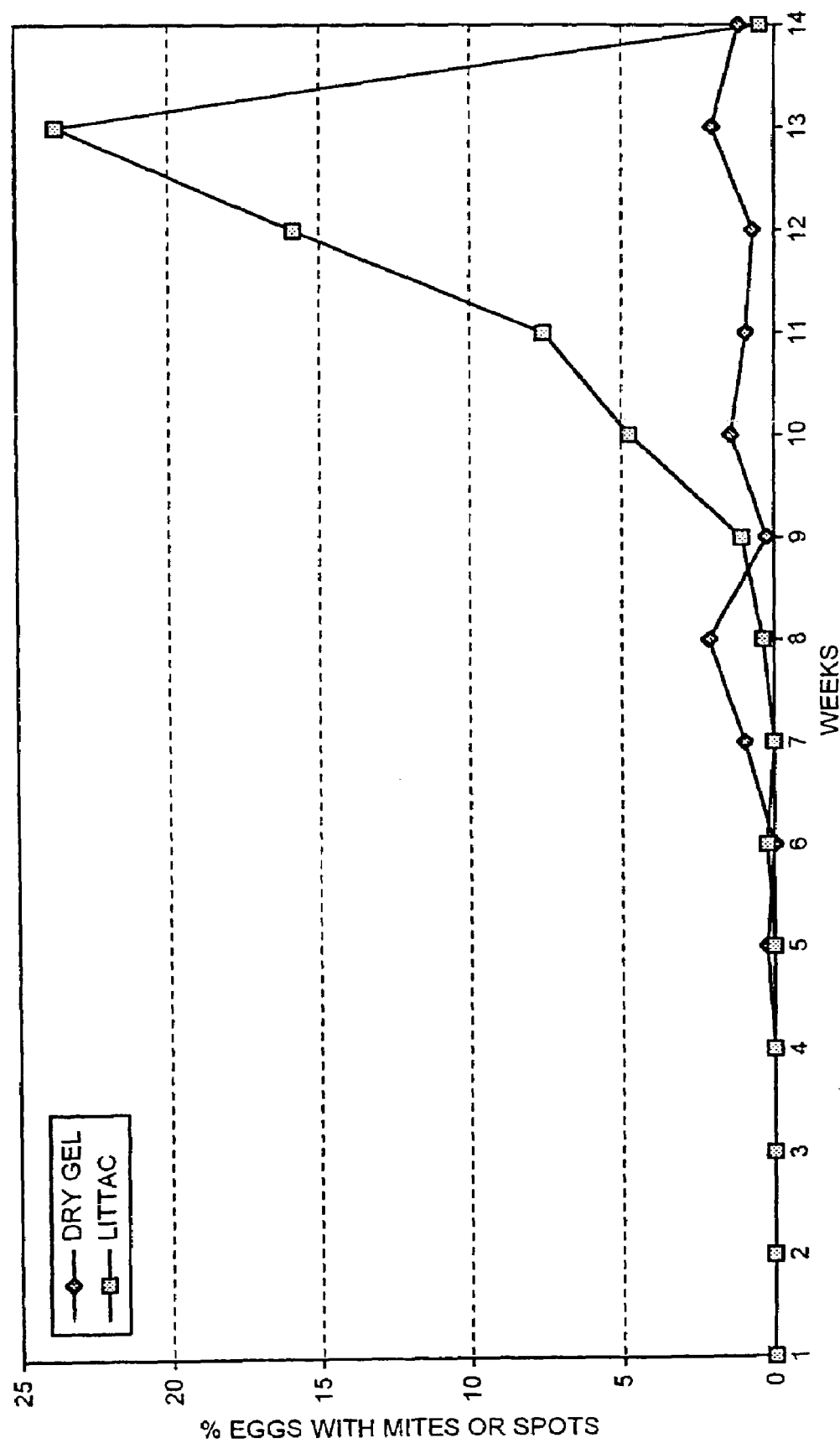
FIG. 1 shows a comparison of the gel composition of the invention and alphacypermethrin ("Littac") against poultry red mite in egg assessments described in Experiment 6.

A discovery on which the present invention is based lies in the use of certain gelling agents which, when added to a premix formed by mixing the water and a specific type of hydrophobic silica under high shear conditions and then mixed with the premix also under high shear conditions, give a storage-stable aerated gel composition. Many conventional gelling agents which are ordinarily used to gel aqueous systems do not produce storage-stable gel compositions according to the present invention. The reasons for this are not, at present, understood.

Where the words "comprises" and "comprising" are used herein, it is intended that these may have the meanings "includes" and "including", respectively, to the extent that the presence of one or more other materials is not excluded.

The aerated gel composition comprises a fine particulate hydrophobic silicone-treated silica having a surface area of from 80 to 300 $m^2/g$. By the term "fine particulate", as applied to the hydrophobic silica, it is meant that the hydrophobic silica will typically have an average particle size of less than 40 $\mu m$. The silica used is one that has been rendered hydrophobic by surface treatment using one or more organosilicon compounds to produce, on the silicon dioxide surface, silicone groups. The technique of hydrophobicizing silica in this way is well-known and such silicone-treated silica is available commercially. We have found that good results are obtained by using hydrophobic silica marketed under the name CAB-O-SIL ("CAB-O-SIL" is a trademark of Cabot Corporation), preferably CAB-O-SIL TS720. However, other silicone-treated silicas can also be used in the present invention if they have a surface area within the range of from 80 to 300 $m^2/g$. The hydrophobic silica may also be one that has been surface treated to produce siloxane, as well as, silicone groups attached to the silicon dioxide surface.

The hydrophobic silica is used in an amount of from 2 to 5% by weight based on the total weight of the composition. The use of greater than 5% by weight of the hydrophobic silica results in a gel composition which is excessively dusty. The use of such a composition may give rise to a greater nuisance dust risk. Preferably, the amount of hydrophobic silica will be in the range of from 3 to 4% by weight of the composition.

The water used may typically be tap water although purified grades may be appropriate for some applications. The water will normally be used at ambient temperature since there appears to be no advantage in using heated or cooled water in the performance of the invention. The water generally will form from 30 to 97% by weight of the total composition. Preferably, however, the amount of water will be from 90 to 97% by weight to ensure the formation of aerated gel compositions of good consistency and improved stability.

As mentioned above, the gelling agent is one or more selected from xanthan gum, sodium alginate and neutralised carboxyvinyl polymers, such as carboxypolymethylene neutralised with triethanolamine. These gelling agents are included in an amount of from 0.2 to 5% by weight. The use of an amount greater than 5% by weight of the gelling agent results in a gel composition having an excessively high gel strength. Preferably from 0.5% to 2%, by weight of the gelling agent will be used depending on the desired stability and structure of the gel composition. Other hydrophilic or hydrophobic additives known to those skilled in the art may be incorporated to modify the physical or biological properties of the composition.

The process for producing the gel compositions involves mixing the water with the silica under high shear conditions typically for a few minutes, for example. 2 to 5 minutes. The mixing at this stage in the process must be carried out under high shear conditions, i.e., conditions cause the water to be finely fragmented into minute droplets which become dispersed within the finely particulate hydrophobic silica such that the surfaces of the water droplets become coated with the hydrophobic silica particles. The term "high shear" is, of course, well-known to the person skilled in the art of mixing or blending and whether or not a particular mixing apparatus is capable of mixing aqueous compositions under high shear conditions will be known to one skilled in the art. This may be achieved by using standard high speed mixers, typically using a mixing speed of at least 2000 rpm and generally from 2000 to 3000 rpm. After the hydrophobic silica and the water have been mixed to create a dispersion of fine droplets of water in the silica, the gelling agent is added and mixing at high speed is continued for several minutes until the gelling agent has been thoroughly incorporated into the liquid phase. It is preferred in the present invention to add the gelling agent after the silica and water have been thoroughly mixed together. If the gelling agent is added before the silica, mixing requires more energy and the homogeneity and stability of the resulting gel composition can be compromised.

The aerated gel compositions described herein have activity against a variety of pests, particularly insects and acarids, for example, mites such as Poultry Red Mite (*Dermanyssus gallinae*), termites (*Reticulitermes* sp.), housefly (*Musca domestica*), beetles and cockroaches. Although we do not wish to be bound by theory, we believe that the aerated gel composition is effective against pests because of the tendency of the composition to stick to the body, particularly the legs, of the pest so as to render the pest immobile and also because the silica in the composition physically damages the epicuticular wax layer on insects and mites. The components of the composition are not toxic and are not believed to have a detrimental effect on the environment generally or be toxic to other life forms that may come into contact with the composition. Also, because the main cause of action against pests is mechanical, rather than chemical, treated pests do not become tolerant or resistant to the composition of the invention.

The compositions are properly sprayable like liquids using conventional spraying equipment, unlike known pulverulent dry water compositions. The compositions do not normally cause any blocking of nozzles in the spraying equipment unlike known pulverulent dry water compositions although in the event that any blocking does occur the equipment can simply be washed with water, e.g., tap water, to remove the blockage. The water content of the aerated gel composition makes it possible to spray the composition with intended direction, over large distances and enables the composition, when sprayed, to stick to the target. Contrariwise, pulverulent compositions cannot be sprayed far or with any great degree of direction and are less likely to stick to the target.

The storage-stable pesticidal compositions of the present invention can be used in formulations produced for domestic, veterinary, agricultural and horticultural applications.

The invention will now be illustrated by the following examples in which the compositions in Examples 1 to 3 and 5 to 7 were mixed using an IKA RE166 high speed mixer having a radial flow toothed disc mixer head and the composition in Example 4 was mixed using a larger scale Torrance high speed mixer having a radial flow toothed disc mixer head.

EXAMPLE 1

Cold tap water 95.5 g was mixed with 3 g of CAB-O-SIL TS720 (silica) at 2800 rpm on the laboratory mixer for 2 minutes. "Dry water" was not formed. Powdered xanthan gum 1.5 g was added and the mixer speed increased to 5500 rpm for a further 3 minutes. A free-flowing aerated gel was formed with a density of 0.6 g/ml. No water separated on storage at laboratory ambient (max/min 30/8° C.) at 24 weeks.

EXAMPLE 2

Cold tap water 96.5 g was mixed with 3 g of CAB-O-SIL TS720 at 2800 rpm on the laboratory mixer for 2 minutes. "Dry water" did not form. Powdered xanthan gum 0.5 g was added and the mixer speed increased to 5500 rpm for a further 3 minutes. A free-flowing aerated gel was formed similar in appearance to that formed in Example 1. The gel composition formed in this Example could be syringed through a 0.26 mm internal diameter needle but blocked a 0.21 mm internal diameter needle.

EXAMPLE 3

Using a larger mixing vessel with the laboratory mixer 1930 g of cold tap water, 60 g of CAB-O-SIL TS720 and 10 g of powdered xanthan gum were mixed by the same process as described in Example 2. The product was identical to that produced in Example 2. A 1 liter sample was transferred to a 2 liter PET bottle and held under 1.7 bar pressure. This sample remained stable with no water separation for greater than 31 days stored at ambient temperature. Some water separation was noted after 59 days under continuous pressure. The sample was easily re-homogenised by 5 vigorous inversions and no further water separated until 16 hours later.

EXAMPLE 4

Cold tap water 77.2 kg was mixed with 2.4 kg of CAB-O-SIL TS720 on the production mixer at 2500 rpm for 1 minute. "Dry water" did not form. Powdered xanthan gum 0.4 kg was added and mixing continued at the same speed for a further 10 minutes. The product was a free-flowing aerated gel as in Examples 1 to 3. Six further 80 kg batches were made by the same process and recipe without variation in the product. A sample of this product 8.6 kg was packed into a polypropylene bucket with a tightly fitting lid. This sample was transported in a car for 2022 miles over a duration of 6 weeks. No water separation occurred during this period. At 14 weeks there was 4.7% m/m water separation. Further samples from these production batches were applied as a "wet dust" through a GLORIA 2010 Knapsack sprayer at 2 to 4 bar pressure fitted with a TEEJET 65030E brass nozzle. The nozzle filter was removed for these applications. A total of 115 liters of dry gel were applied through this knapsack sprayer without blockage. Further samples were applied as a "wet dust" through a STIHL SR400 motorised mistblower fitted with a pressure pump. The tank filter was removed and the standard adjustable spray nozzle was retained for these applications. A total of 250 liters of dry gel was applied through this mistblower at a nozzle setting of 3 to 4 without blockage.

EXAMPLE 5

Cold tap water 76.5 g, propylene glycol 20 g and 3 g of CAB-O-SIL TS720 were mixed on the laboratory mixer at 2800 rpm for 2 minutes. "Dry water" did not form. Powdered xanthan gum 0.5 g was added and the mixing speed increased to 5500 rpm for a further 3 minutes. The product was a free-flowing aerated gel of a wetter consistency than in Examples 1 to 4. No water separation occurred after 5 days ambient storage.

EXAMPLE 6

Cold tap water 96.3 g and CARBOPOL 980® (registered trademark of BF Goodrich Co.) 0.5 g (a carboxyvinyl polymer) were mixed on the laboratory mixer at 2800 rpm for 1 minute. CAB-O-SIL TS720 3 g was added and mixed at the same speed for a further 2 minutes. "Dry water" did not form. Triethanolamine 0.2 g was added to neutralise the CARBOPOL and the mixing speed increased to 5500 rpm for a further 3 minutes. A thick pliable aerated dry gel was formed that could be easily extruded through a 30 ml plastic syringe. No water separation occurred after 13 weeks ambient storage.

EXAMPLE 7

Cold tap water 96 g and 3 g of CAB-O-SIL TS720 were mixed on the laboratory mixer at 2800 rpm for 2 minutes. "Dry water" did not form. Sodium alginate, high viscosity grade, 1 g (a polysaccharide) was added and the mixing speed increased to 5500 rpm for a further 3 minutes. A free-flowing aerated gel was initially formed which thickened to a non-flowing gel after 5 days. The gel remained pliable and could easily be extruded from a 30 ml plastic syringe. No water separation occurred after 6 days ambient storage.

EXAMPLE 8

Investigation into the Moisture Absorption Properties of the Dry Gel Composition A. Preparation of Test Samples Test Sample 1

A dry gel composition according to the invention was prepared as described in Example 2 above. This dry gel composition contained, as % by weight based on the total weight of the composition, 96.5% of water, 3.0% by weight of CAB-O-SIL TS720 and 0.5% of xanthan gum.

Test Sample 2

Cold tap water 96.5 g was mixed with 3 g AEROSIL 200 (a hydrophilic silica) at 2800 rpm on the laboratory mixer for 2 minutes. Powdered xanthan gum 0.5 g was added and the mixer speed increased to 5500 rpm for a further 3 minutes to give the sample formulation.

B. Experimental 10 g of each test sample were weighed into an open glass jar. Each jar was placed in an oven at 80° C. for 6 hours to evaporate the water from each formulation. The weight of the dried residues was recorded. Each jar containing dried residue and also an untreated control jar were weighed and transferred to an oven at 30° C. held for 4 days at >90% relative humidity in a sealed container. Each jar was then weighed and the weight gain for each was calculated. The weight gain of the untreated control jar was subtracted from that of each jar containing dried residue to give an adjusted weight gain of each dried residue. This adjusted weight gain was expressed as a percentage gain over the respective initial dried residue weight. The results are shown in the Table below.

C. Table

| Formulation | Sample wt. g | Dry wt. g | Wt. Gain g | Adjusted gain g | % gain over dry wt. |
|---|---|---|---|---|---|
| Test Sample 1 (invention) | 10.0138 | 0.6588 | 0.0053 | 0.0011 | 0.1670 |
| Test Sample 2 (comparison) | 10.0185 | 0.3287 | 0.2204 | 0.2162 | 65.7743 |
| Control | — | — | 0.0042 | — | — |

D. Conclusion

The dry residues of the dry gel composition of the invention absorbed very little moisture in the test. These residues, therefore, cannot act as a desiccant material. In contrast, the dry residues of the AEROSIL 200—containing composition (Test Sample 2) underwent a substantial weight gain as the result of moisture absorption in the test and, thus, have desiccant properties.

There now follows a series of Experiments illustrating the pesticidal activity of the composition of the invention.

Experiment 1

Poultry Red Mite (*Dermanyssus gallinae*)

Forced Exposure Test

Method:

The aerated gel composition prepared according to Example 2 above was applied to three replicate 9.0 cm diameter filter papers so that the total surface was coated (approximately 3 ml of formulation). The papers were left to dry at room temperature. Three further papers were also set-up as above except these were used for the study while still wet.

Twenty mites (mixed age and sex) were placed on each of the six test papers. Control papers were untreated, three dry and three wet (water only) again each infested with 20 mites.

Results:

The mites were unable to walk on either a wet or a dry deposit of the aerated gel composition—the ends of the tarsi rapidly became covered in silica and mites were knocked-down (KD) 100% in <10 minutes—unable to right themselves. This was followed by 100% mortality (M) in 2 hours. There was no mortality in the control dishes by 24 hours.

Choice Exposure Test

Method:

A choice test was designed so that the mites had access to untreated cracks and crevices. A 9.0 cm diameter petri dish was set-up to contain a crumpled piece of filter paper—this provided many harbourages for the mites. Part of the paper received a treatment of the composition prepared in Example 2, the rest was left untreated. Three replicate dishes were set-up. Control dishes were set-up as per test dishes except that they contained untreated paper.

Results:

All of the mites in the test dishes had silica on them after 2 hours. The paper harbourage was totally damp by this time as it had absorbed water from the formulation—this provided a very favourable environment for mite survival. After 3–4 hours there was 80% KD. The test was left running overnight as there were still some mites deep inside the harbourages. After 24 hours there was 100% M in all test dishes and 0% M in the control dishes.

Choice and Forced Exposure Tests on Metal Surfaces

As the predominant surface in poultry houses (battery) is metal, studies were carried out to determine the efficacy of the composition of the invention.

Choice Test:

A choice test consisted of a 4.0 cm diameter circle of the composition prepared in Example 2 pipetted onto a metal sheet. Twenty mites (mixed age and sex) were placed inside the circle on the untreated metal. Three replicates were set-up. Three untreated controls were also set-up.

Forced Exposure Test:

A thin layer of the gel composition of Example 2 was smeared onto the metal and was then infested with 20 mites (mixed age and sex). Three test replicates were set-up and three replicate controls.

Results:

For both the Choice and the Forced Exposure tests there was 100% KD in 15 minutes followed by 100% M in 2 hours. There was 0% M in the controls.

Mode of Action

The gel composition sticks to the mites bodies, especially the ends of their legs (tarsi) which gets covered to the extent that the mites are unable to walk or move normally. They rapidly (in 10 to 15 minutes) fall onto their backs and are immobilised. This is purely mechanical action. Once on their backs they are unable to right themselves and die.

An experiment was set-up to investigate the mode of action—how did the mites die once immobilised?

Method:

Four groups of mites were set-up as follows:

Group 1:

Twenty mites were exposed to the gel composition of Example 2 until they became knocked-down. They were then left on the laboratory bench exposed to the air. The humidity in the laboratory was 35% RH.

Group 2:

As Group 1 except that these mites were kept at 95% RH after KD. (This humidity was achieved in a humidity chamber containing saturated salt solution).

Group 3:

Control group—as Group 1 except that these mites were not exposed to the gel composition. Humidity as Group 1: 35% RH.

Group 4:

Control group—as Group 2 except that these mites were not exposed to the gel composition. Humidity as Group 2: 95% RH.

All groups were assessed for knock-down and mortality after 24 hours.

Results:

Group 1:
100% M—all mites dead at 24 hours.

Group 2:
All mites were immobilised on their backs but very actively moving their legs. These mites were still alive after 72 hours, however, they were still immobilised. After 72 hours these mites were transferred to a humidity of 35% RH—death was rapid 100% M<2 hours.

Group 3:
All mites were alive but were showing strong clumping behaviour alternated by periods of active moving around.

Group 4:
All mites were alive and actively moving around.

Summary

1. The gel composition mechanically immobilises the mites by attaching to and clogging up the ends of the legs (the tarsi).
2. The gel composition either removes or alters the waxy cuticle, so that unless in an extremely high humidity environment, the mites rapidly die. Although we do not wish to be bound by theory, we believe that the physical damage caused to the epicuticular wax on the mites results in a hydrostatic imbalance and death. Once immobilised by the formulation the mites remain immobilised even if they are in a very humid environment.

Experiment 2

Termites (*Reticulitermes* sp.)

Forced Exposure Test

Method:

Three replicate dishes were set-up as follows: the gel composition prepared in Example 2 was applied to a 9.0 cm diameter filter paper to give an even deposit. (Approximately 3 ml of composition was applied to the paper). The paper was placed into a plastic petri dish and 10 termites were placed onto the treated surface. Control dishes were set-up exactly the same except that only water was applied to the paper.

Results:
Test—100% M in 2 hours. Controls—0% M in 20 hours.

Choice Exposure "Tank Test"

Method:

A fresh piece of wood was placed in a termite laboratory culture on a bed of the gel composition prepared in Example 2 so that the gel composition formed a barrier between the soil and the wood. Control wood was also placed on the soil—(the wood was in direct contact with the soil). The culture was checked after 3 hours, 24 hours and 72 hours.

Results:

3 Hours:

Test wood—no termites on any part of the wood.

Control wood—the under surface of the wood, where it was in contact with the soil, was totally covered with termites and the insects were beginning to make soil tunnels up the side of the wood.

24 Hours:

Test wood—evidence of termite activity around edge of the gel composition but not in contact with either the wood or the gel composition.

Control wood—soil tunnels were over the sides and top of the wood and underneath it.

72 Hours:

Test wood—the termites had built a soil tunnel "bridge" over to the top of the wood so as to avoid any contact with the gel composition.

Control wood—the wood was no longer visible as it was totally covered with soil and termites.

Experiment 3

Housefly (*Musca domestica*)

Choice Exposure Test

Method:

0.5 ml of the gel composition prepared in Example 2 was applied to the edge of three replicate 9.0 cm diameter filter papers so that only a small section of each filter paper was coated.

Ten adult housefly, WHO susceptible strain, (mixed sex) were placed on each of the test papers. Control papers were untreated, again each infested with ten adult housefly. The test was repeated using a resistant strain of housefly zb 381 ex. Danish Pest Infestation Laboratory. this strain had been kept under continuous pressure with Dimethoate and Permethrin.

Results:

Test papers—for both strains there was 100% KD by 5 hours followed by 100% M by 12 hours.

Control papers—no KD or M.

Cage Choice Exposure Test

Method:

A laboratory cage test was set-up as follows with the only treated area being a short length of string:

A 30×30×30 cm fly cage was infested with 50 mixed sex houseflies and a water pad and dish of sugar was provided. A 12 cm string coated with the gel composition of Example 2 was suspended internally from the top of the cage. The flies were observed for KD and mortality. The humidity in the laboratory was 35% RH.

Results:

The first signs of KD was recorded after 1 hour (5 flies). There was 86% mortality by 20 hours and 100% mortality by 36 hours.

Mode of Action

No obvious mechanical action such as immobilisation was observed with the houseflies as was observed with the poultry red mite. Even flies totally covered with the gel composition were still able to walk or fly. It was suspected that mortality was occurring due to the physical damage caused to the epicuticular wax on the insects resulting in hydrostatic imbalance and death. To determine the mode of action the following test was carried out.

Method:

Six groups of flies were set-up as follows:

Group 1:

Ten flies were placed in a 9.0 cm petri dish on a filter paper totally coated with a wet deposit of the gel composition used above. The dish was covered with a cotton mesh so that it was open to the air. The dish was left on the laboratory bench at a humidity of 35%. Three replicate dishes were set-up.

Group 2:

As Group 1 except that these flies were kept at 95% RH. (This humidity was achieved in a humidity chamber containing saturated salt solution). Three replicate dishes were set-up.

GROUP 3:

As Group 1 except that these dishes were covered by a plastic petri dish lid instead of cotton mesh—there was, therefore, high local humidity. three replicate dishes were set-up.

Group 4:

Control group—as Group 1 except that these flies were not exposed to the gel composition just a moist filter paper. Humidity as Group 1: 35% RH.

Group 5:

Control group—as Group 2 except that these flies were not exposed to the gel composition just moist filter paper. Humidity as Group 2: 95% RH.

Group 6:

Control group—as Group 3 except that these flies were not exposed to the gel composition just a moist filter paper. Humidity locally high.

All groups were assessed for knock-down and mortality after 24 hours.

Results:

Group 1:

There was 100% M by 17 hours.

Group 2:

There was 0% M by 36 hours. However, as soon as these flies were removed to low humidity of 35% death occurred rapidly—100% M within 2 hours.

Group 3:

There was 20% M by 17 hours, 50% M by 24 hours and 100% M by 30 hours.

Group 4:

Control group—there was no mortality by 24 hours and 20% M by 36 hours.

Group 5:

Control group—there was no mortality by 36 hours.

Group 6:

Control group—there was no mortality by 36 hours.

Summary

Flies kept on a deposit of the gel composition exposed to 35% RH die after approximately 17 hours. However, if an identical dish of flies is kept at 95% humidity there is no mortality by 36 hours even though the flies are totally coated with the gel composition. If these flies are removed from their high humidity to a humidity of 35% death is rapid, 100% M within 2 hours.

These results indicate that the waxy cuticle has been physically damaged and that the flies are no longer able to maintain hydrostatic stability—only being able to survive in extremely high humidity environments. When in a low humidity environment water loss is rapid and death occurs. Files totally covered in the gel composition survive—as long as the humidity remains high—proving that the gel composition itself is not toxic in any way to the flies.

Experiment 4

Little Beetle (*Alphitobius diaperinus*)

Forced Exposure Test

Method:

The gel composition prepared in Example 2 was applied to six replicate 9.0 cm diameter filter papers so that the total surface was coated (approximately 3 ml of composition per paper).

Ten adult litter beetles (mixed sex) were placed on each of three test papers and ten litter beetle larvae were placed on each of the three remaining test papers. Control papers were untreated—three infested with ten adult beetles and three infested with ten larvae.

Results:

Adult beetles—knock-down was slow to occur on the test papers 40% by 24 hours, 80% by 36 hours and 100% by 48 hours. This was followed by 100% mortality.

Larvae—0% KD by 24 hours followed by 100% KD by 30 hours and 100% M by 36 hours.

Experiment 5

Cockroaches

A brief Choice Exposure Test was carried out against German cockroaches (*Blattella germanica*). The results showed that 50% mortality was achieved in 24 hours and 100% mortality was achieved in 72 hours.

Experiment 6

Comparison Between the Gel Composition of the Invention and Alphacypermethrin Against Poultry Red Mite in a Battery Egg Production Unit Aim To compare the activity of the gel composition prepared as described in Example 4 with that of a commercial standard "Littac" (alphacypermethrin 1.47% w/w) against poultry red mite in commercial intensive battery egg production unit.

Site

Previous mite control history: "Micro-mite" (HSE 4480) Fenitrothion 46.77% w/w 50 g/li applied at the rate of 5 liters/100 m² had been used extensively—applied every 3 weeks with poor results.

One house in particular was giving them tremendous problems with red mite control—this house was selected for the trial.

The house consisted of six "batteries". Each "battery" consisted of two sides (side 1 and side 2) back to back of lengths of 112 cages, stacked six cages levels high (a total of 672 cages/side or 1344 cages/battery). The cage levels were labelled alphabetically—the lowest level of cages being "level A" and the highest "level F".

Monitoring Method

Battery 1 was monitored for the gel composition and battery 3 was monitored for the Littac treatment.

For both treatments, the level of mite infestation was monitored using three different techniques.

Egg Assessments

The total numbers of eggs were counted on levels A, B and C on both sides 1 and 2.

The total number of eggs with mites or squashed mites were counted on levels A, B and C on both sides 1 and 2.

The percentage of eggs with mites or squashed mites was determined for each of the two treatments.

A pre-treatment value for this assessment had been determined during previous work in this unit. Post-treatment assessments were carried out at weekly intervals.

Plate Assessments

Mites are first noticed at this site when they begin to emerge from behind the metal plates on the fronts of the cages. These metal plates were used to help to determine the infestation levels of mites on the two treatments.

The metal plates situated on the front of the cages along level B on both sides 1 and 2 were assessed as either having mites present or not having mites present. There were 54 plates on each side, making a total of 108 plates assessed for each treatment. The percentage of plates infested with mites was determined for each treatment. Assessments were carried out at weekly intervals.

Clip Assessments

At this site, when an infestation of mites is particularly heavy, the mites tend to migrate and infest other areas such as the egg conveyer belts and the fronts of the cages followed by plastic clips along the lengths of the egg conveyer belts. Infested plastic clips usually indicate a heavy infestation at this site.

This assessment was carried out to demonstrate the extent of mite migration on the batteries during the course of the trial. The plastic clips on level C on both sides 1 and 2 were assessed as having one of the following categories of mites present:

| CATEGORY | LEVEL OF COLONISATION |
|---|---|
| 1 | No mites |
| 2 | <20 mites |
| 3 | Mites covering both ends of the clip |
| 4 | Mites covering both ends of the clip and its length |
| 5 | Clip totally covered in mites |

This assessment was carried out at weekly intervals.

Treatments

The gel composition of Example 4 was applied to both sides of batteries 1 and 2. Littac was applied to both sides of batteries 3 and 4. The treatments were applied as follows:

1. Initial Treatment—Applied at the Start of the Trial

The gel composition was applied by mistblower, setting 3, to both sides of batteries 1 and 2. Any "difficult" cracks and crevices received an additional knapsack crack and crevice treatment. The application rate was calculated as 1 liter of the gel composition per 12 m². Littac (alphacypermethrin 1.47% w/w) was diluted 200 ml concentrate to 5 liters water/100 m² and was applied by mistblower to both sides of batteries 3 and 4.

2. Spot-treatment—Applied 5 and 13 Weeks after the Start of the Trial

A "spot-treatment" of the gel composition was carried out by knapsack sprayer to both sides of batteries 1 and 2 five weeks after the start of the trial. The composition was applied only to the edge of the metal plates on the fronts of the cages where the mites were emerging from and beginning to form clumps. A further knapsack spot-treatment was carried out at 13 weeks to control clumps forming on the divisions of the cage fronts.

3. Partial Re-Treatment—Applied 8½ Weeks after the Start of the Trial

A partial re-treatment of the gel composition was carried out by mistblower to both sides of batteries 1 and 2 8½ weeks after the start of the trial. The composition was applied only to the fronts of the cages to try to control any clumps of mites formed.

4. Full Re-Treatment—Applied after 10 Weeks after the Start of the Trial

Ten weeks after the start of the trial a full re-treatment of Littac (same as the initial treatment of Littac) was carried out by mistblower to both sides of batteries 3 and 4.

5. Full Re-Treatment—Applied after 13 Weeks after the Start of the Trial

Thirteen weeks after the start of the trial a full re-treatment of the gel composition was carried out by mistblower to both sides of batteries 3 and 4 (the previous Littac treatment).

Results

Egg Assessments

All egg assessment results are shown in FIG. 1.

The invention—the percentage of eggs with mites on them remained below 2% during the 15 weeks of the trial (Pre-treatment assessments of mites on eggs ranged from 42% to 76% with a mean of 57% of eggs with mites on them).

Littac—the percentage of eggs with mites on them remained below 2% during the first 9 weeks of the trial. At 10 weeks 4.8% of the eggs had mites on them—a total re-treatment was carried out at 10 weeks. The number of mites continued to rise rapidly—by 13 weeks 24% of the eggs had mites on them and the surface of the cages and egg conveyers were "crawling" with mites—very mobile.

A sample of mites were tested for resistance to Littac at the laboratory and the speed of action was very slow with time to knock-down approximately 6 hours rather than 20 minutes suggesting that a degree of tolerance was developing after only 1 application.

The Littac batteries (3 & 4) received a treatment of the gel composition by mistblower at 13 weeks and within 3 days the level of mites on the eggs had decreased to 0.5% and the only mites visible were some clumps of mites around the cracks on the metal plates.

Plate Assessments

Figure 2:
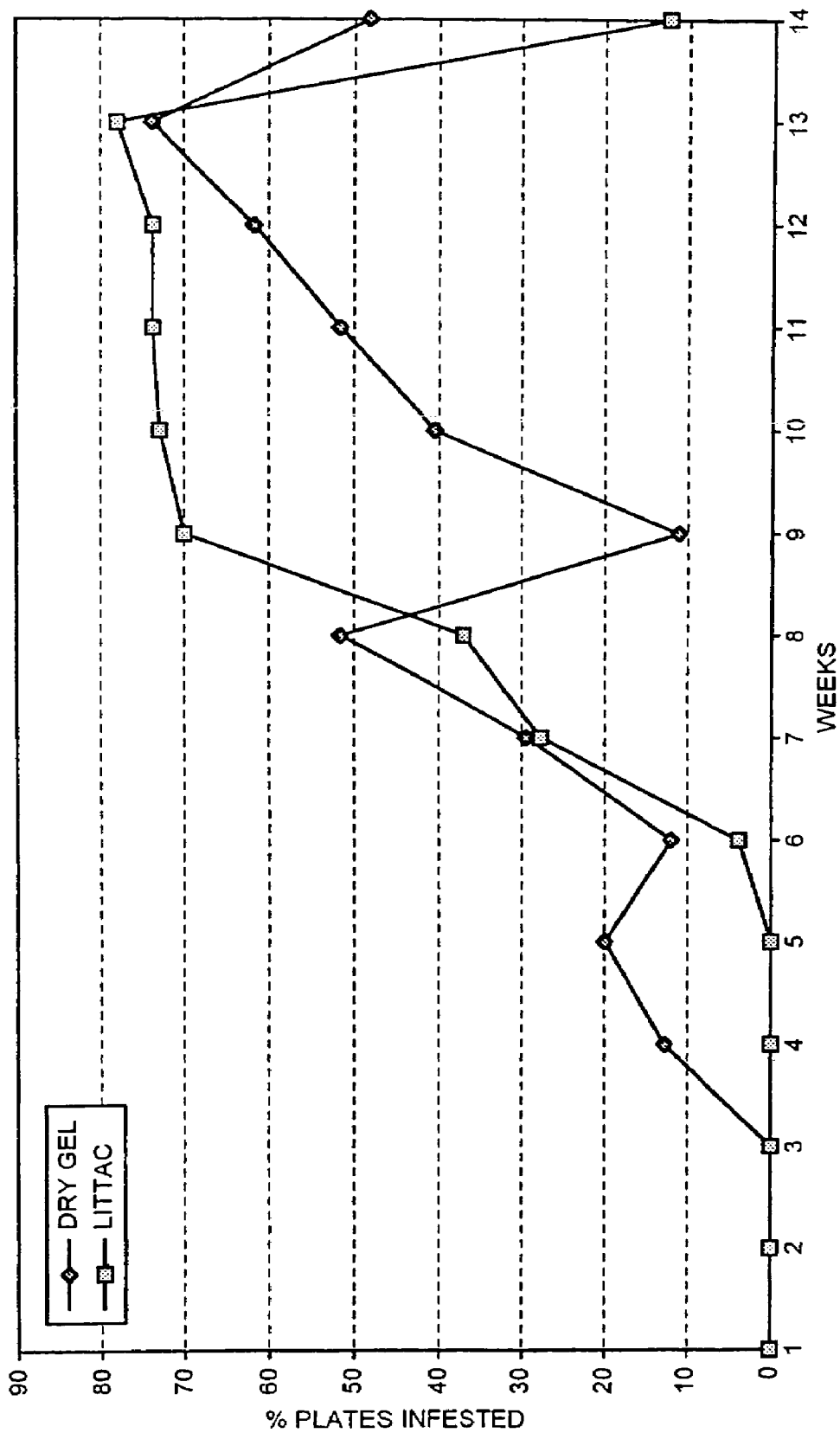
FIG. 2 shows a comparison of the gel composition of the invention and Littac against poultry red mite in plate assessments described in Experiment 6.

All plate assessment results are shown in FIG. 2.

The invention—mites began emerging from behind the plates by week 4, with 20% of plates infested by week 5. There was a minor "spot" re-treatment by knapsack to cracks and crevices around the plates carried out at 5 weeks. Plate infestation dropped to approximately 12% by week 6. The number of plates infested, however, continued to rise over the following 2 weeks reaching to over 50% by week 8. Because of this there was only a re-treatment to the cage fronts carried out at 8½ weeks by mistblower. By week 9 only 11% of the plates were infested. The percentage of plates infested began to rise again—by week 13 over 70% of the plates were infested. There was a further minor "spot" re-treatment by knapsack to cracks and crevices around the plates carried out at 13 weeks—the number of plates infested had fallen to about 48% by the following week.

Littac—mites began emerging from behind the plates by week 6, with 4% of the plates recorded as infested. The percentage of plates infested increased weekly with 73% of plates infested by week 9. By week 10 this had risen to 74%, and as the number of mites on the eggs had increased by this time a full re-treatment of Littac was carried out. By week 13, 78% of the plates were infested with mites, and 23.7% of the egg had mites on them. Following these results the Littac batteries (3 & 4) received a dry water treatment by mistblower at 13 weeks and within 3 days only 12% of the plates had mites.

Clip Assessments

The Invention

Figure 3:
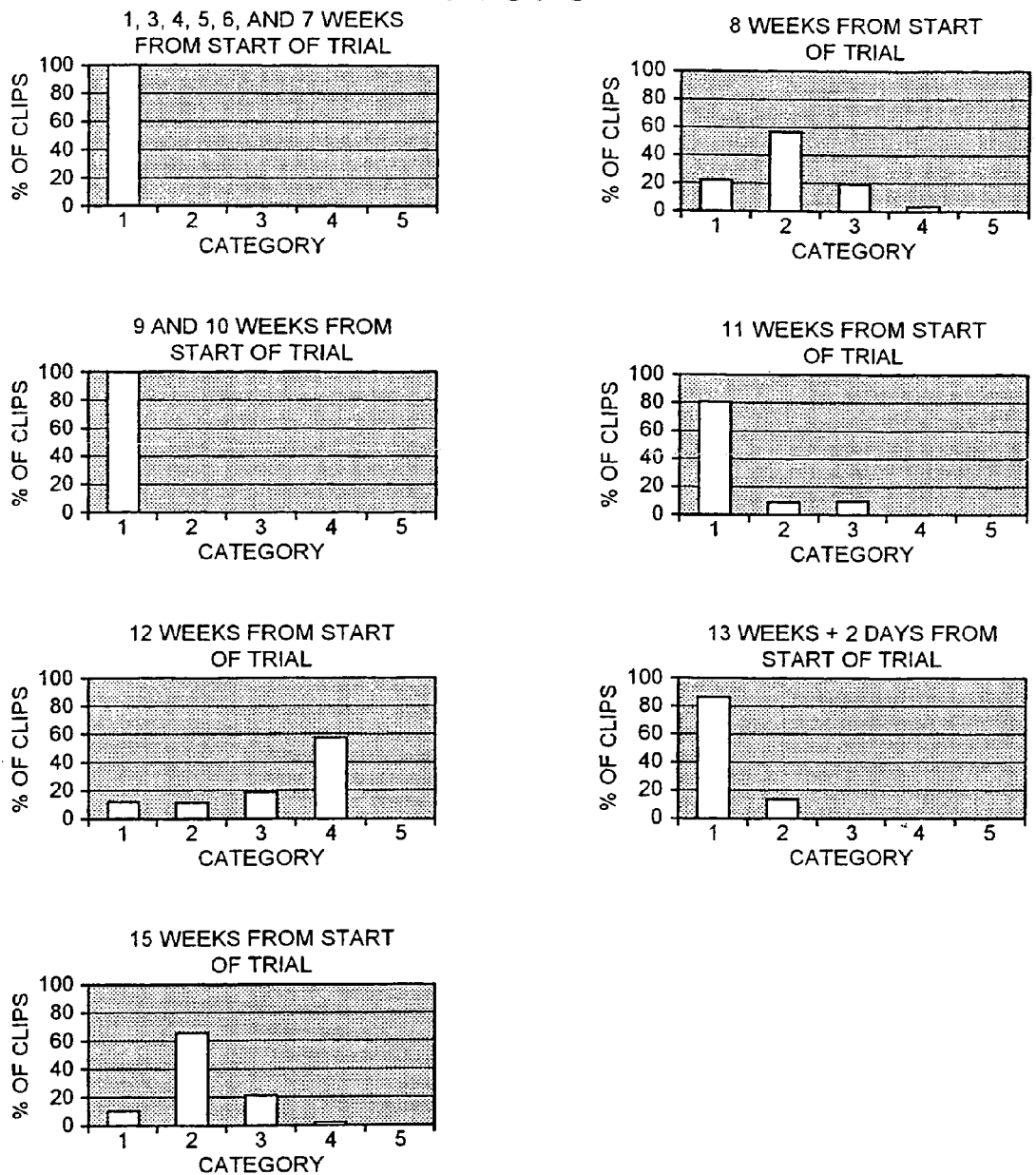
FIG. 3 shows the results of clip assessments described in Experiment 6 using the gel composition of the invention against poultry red mite.

All clip assessment results for the treatment are shown in FIG. 3.

All plastic clips remained clear of mites for the first 7 weeks of the trial. By 8 weeks 60% of the clips were infested with <20 mites/clip. the re-treatment of the cage fronts (including the clips) was carried out at 8½ weeks and this reduced the clip infestation to zero. This was maintained for almost 3 weeks.

By week 12 almost 60% of the clips had mites infesting both ends plus the length of the clips (category 4). A knapsack re-treatment to plates and clips only was sufficient to reduce the clip infestation to 82% of the clips having no mites, the remaining clips having <20 mites. Clip infestation was beginning to rise again by week 15.

Regular spot re-treatments would be required in order to maintain control of mites on the clips.

Littac

All clip assessment results for the Littac treatment are shown in FIG. 4.

All plastic clips remained clear of mites for the first 7 weeks of the trial. By 8 weeks 60% of the clips were clear of mites but 26% of the clips were classed as category 4. By 9 weeks clip infestation had increased further and a re-treatment of Littac occurred at 10 weeks. Following this re-treatment clip infestation continued to rise and by 12 weeks >60% of the clips had an infestation greater than category 3. The gel composition was then applied to batteries 3 and 4 and this achieved approximately 80% of clips clear of mites and the remaining 20% with <20 mites on.

Conclusion—Effectiveness of the Gel Composition of the Invention

Excellent control of mites on eggs—<2% of the eggs infested with mites compared with a mean of 57% infested pretreatment.

Although the eggs have been kept clear of mites, there are still clumps of mites on the cage fronts and around cracks and crevices. These clumps are proving difficult to break up with the gel composition of the invention as only the mites on the outside of the clump come into contact with the composition.

Regular re-treatments would be required to control development of the clumps.

Experiment 7

Comparison Between the Gel Composition of the Invention and Alphacypermethrin Against Poultry Red Mite in a Free Range Egg Production Unit Aim To compare the activity of the gel composition prepared as described in Example 4 with that of a commercial standard "Littac" (alphacypermethrin 1.47% w/w) against poultry red mite in commercial free range poultry egg production units.

Site

The farm consisted of both battery and free-range egg production units. Two separate free range units were selected for use in this trial.

House 1 measured approximately 140×140 ft. and had central nest box areas occupying the length of the house measuring 6×140 ft. with 45 nest boxes down each side. House 2 was similar but had two levels of nest boxes.

Previous mite control history: Fenitrothion WP had been used extensively with poor results. The farmer's perception was that it was "not working".

The houses were selected to receive the following treatments:

| | |
|---|---|
| House 1: | The gel composition of the invention was applied at the start of the crop by mistblower blanket application. |
| House 2: | LITTAC applied mid-crop by knapsack - crack & crevice treatment. |

Monitoring Method

The level of mite infestation was monitored using mite traps (corrugated plastic, 1×3 cm). In each house the traps were placed every third nest box under the wooden covering to the egg conveyer belt. This trap position was selected due to the high activity of mites in that area. Traps were left in place for 48 hours after which they were removed to sealed glass jars and transported to the laboratory for assessment.

At the laboratory the mite population was assessed by calculating the weight of the mites in the traps.

In house 1 mite trap assessments were carried out one week before treatment and 1, 2, 3, 4, 6, 8 and 10 weeks post-treatment.

In house 2 mite trap assessments were carried out one week before treatment (pre-treatment assessment) and at 1, 2, 3, 4, 5, 6, 7, 8, 9 and 10 weeks post-treatment.

Application

House 1—The Gel Composition of the Invention Applied at the Start of the Crop Cycle The gel composition of Example 4 was applied by mistblower on setting 3 to 4. The application rate was calculated as 1 liter formulation per 12 $m^2$. The application was a mixture of blanket application to the nest box area and a crack and crevice treatment.

House 2—"Littac" Applied Mid-Crop Cycle

"Littac" (alphacypermethrin 1.47% w/w) was diluted by adding 200 ml concentrate to 5 liters water and was applied by a Cooper Peglar CP3 knapsack fitted with a 04-F80 nozzle. The application rate was calculated as 1 liter diluted formulation per 12 $m^2$. The application was primarily a crack and crevice treatment and this accounts for the high application rate used.

Results

House 1—The Gel Composition of the Invention Applied at the Start of the Crop Cycle 100% control was maintained up to 12 weeks post-treatment.

House 2—"Littac" Applied Mid-Crop Cycle

Greater than 95% control was achieved for the duration of the trial—10 weeks.

The results achieved in House 1, i.e., 12 weeks of control after only one application at the start of the crop cycle, are excellent. Mid-crop treatments would require re-treatments every 4 weeks. Many farms carry out insecticide treatments, using conventional insecticides, every 3 weeks to control red mite.

What is claimed is:

1. A pesticidal composition comprising, as the sole pesticidally-active component, a storage-stable aerated gel composition comprising 30 to 97% by weight of water, 0.2 to 5% by weight of a gelling agent selected from xanthan gum, sodium alginate and neutralized carboxyvinyl polymer and 2 to 5% by weight of a fine particulate, hydrophobic silicone-treated silica having a surface area of from 80 to 300 $m^2/g$ which said composition is in the form of fine particles of an aqueous gel containing the water and gelling agent, the surfaces of which fine particles are coated with a coating of the finely particulate hydrophobic silica.

2. A composition according to claim 1, comprising from 90 to 97% by weight of water.

3. A composition according to claim 1, comprising from 3 to 4% by weight of the silica.

4. A composition according to claim 1, wherein the gelling agent is xanthan gum.

5. A method of controlling pests, comprising contacting the pests with the pesticidal composition of claim 1 to control the pests.

6. A method according to claim 5, wherein the pests are selected from insects and acarids.

7. A method according to claim 6, wherein the pests are selected from *Dermanyssus gallinae, Reticulitermes* sp. and *Musca domestica*.

8. A method according to claim 5, further comprising applying directly the pesticidal composition to the pests.

9. A method according to claim 5, further comprising applying the pesticidal composition to a surface to be contacted by the pests.

10. A method according to claim 8, further comprising applying the pesticidal composition by spraying.

11. A method according to claim 7, further comprising applying the pesticidal composition to a surface to be contact by the pests.

12. A composition according to claim 2, comprising from 3 to 4% by weight of the silica.

13. A composition according to claim 2, wherein the gelling agent is xanthan gum.

14. A composition according to claim 3, wherein the gelling agent is xanthan gum.

15. A method of controlling pests, comprising contacting the pests with the pesticidal composition of claim 2 to control the pest.

16. A method of controlling pests, comprising contacting the pests with the pesticidal composition of claim 3 to control the pest.

17. A method of controlling pests, comprising contacting the pests with the pesticidal composition of claim 4 to control the pest.

18. A method according to claim 6, further comprising applying directly the pesticidal composition to the pests.

19. A method according to claim 7, further comprising applying directly the pesticidal composition to the pests.

20. A method according to claim 6, further comprising applying the pesticidal composition to a surface to be contact by the pests.

* * * * *